United States Patent [19]

Tiefnig

[11] Patent Number: 5,583,426
[45] Date of Patent: Dec. 10, 1996

[54] METHOD AND APPARATUS FOR DETERMINING CORROSIVITY OF FLUIDS ON METALLIC MATERIALS

[76] Inventor: Eugen Tiefnig, A-1170 Wien, Rokitanskygasse, Vienna, Austria

[21] Appl. No.: 229,449

[22] Filed: Apr. 18, 1994

[30] Foreign Application Priority Data

Apr. 16, 1993 [AT] Austria ........................ 760/93

[51] Int. Cl.⁶ .................................. G01N 27/00
[52] U.S. Cl. .................. 324/71.2; 324/228; 204/404
[58] Field of Search ........................ 324/220, 228, 324/229, 71.2, 425, 529, 557, 559; 204/148, 153.11, 197, 404; 73/86

[56] References Cited

U.S. PATENT DOCUMENTS

| | | | |
|---|---|---|---|
| 4,019,133 | 4/1977 | Manley et al. | 324/71.2 |
| 4,061,965 | 12/1977 | Nelson | 324/29 |
| 4,328,462 | 5/1982 | Jensen | 324/71.2 |
| 4,468,613 | 8/1984 | Slough et al. | 324/71.2 |
| 4,806,850 | 2/1989 | Saumade et al. | 324/71.2 |
| 4,843,319 | 6/1989 | Lara | 324/71.2 |
| 5,087,873 | 2/1992 | Murphy | 324/71.2 |
| 5,126,654 | 6/1992 | Murphy | 324/71.2 |
| 5,132,620 | 7/1992 | Rempt | 324/244.1 |
| 5,188,715 | 2/1993 | Chen | 204/153.11 |

*Primary Examiner*—Kenneth A. Wieder
*Assistant Examiner*—Glenn W. Brown
*Attorney, Agent, or Firm*—Joseph H. Taddeo

[57] ABSTRACT

A method and apparatus for determining the corrosivity of fluids on a metallic material by means of a coil with AC current with predetermined frequency, amplitude, wave form and range, and a metallic specimen with composition identical to the metallic material exposed to the fluid. The specimen, held within the magnetic field of the coil, sustains loss of mass by exposure to the fluid media with concomitant change in the magnetic quantities of inductivity and inductive resistance. Such changes are then converted from analog to digital, measured, collected and processed by a microprocessor.

45 Claims, 3 Drawing Sheets

METHOD AND APPARATUS FOR DETERMINING CORROSIVITY OF FLUIDS ON METALLIC MATERIALS

REFERENCE TO PREVIOUSLY FILED APPLICATIONS

Your applicant respectfully claims the benefit of an earlier patent filing date in a foreign country. This applicant claims foreign priority pursuant to 35 U.S.C. 119 and 37 CFR §1.55(a), for the Austrian (national) patent, identified as follows:

date of filing the Austrian (national) patent: Apr. 16, 1993;
Austrian Patent Office reference number: A760/93-1;
International Patent Classification: GO1N;
Inventor: Eugen Tiefnig;
Original Title: Verfahran und Vorrichtung zur Ermittlung der Korrosivitat (Method and Device for Determining Corrosivity)

FIELD OF THE INVENTION

This invention concerns a new procedure and equipment to measure corrosion of metallic materials exposed to fluid media. More particularly, the invention relates to measurement of corrosion, especially electrochemical corrosion and erosion of iron alloys in moving fluids.

BACKGROUND OF THE PRESENT INVENTION

Electrochemical corrosion pertains to destruction of the surface of a metal by electrochemical reaction. Such corrosion occurs if an electrolytic solution contacts the junction of two different metals. The corrosion element may be termed a short-circuited galvanic element.

On the element's anode, the less noble metal is oxidized. At the cathode, oxygen or hydrogen ions are reduced. Oxygen corrosion occurs in a neutral or alkali solution; while hydrogen corrosion is the result in solutions of higher pH or acidic solutions.

Electrochemical corrosion is a threat wherever two metallic conductors are in contact. Even foreign elements on a metallic surfaces may cause electrochemical corrosion. A film of water can be sufficient for electrolyte formation by exposure of metallic surfaces to the atmosphere. The rate of electrochemical corrosion is dependent upon conductivity of the electrolyte. Carbon dioxide absorption from ambient air can be partially transformed to carbonic acid in water, thereby contributing to electrochemical corrosion. Industrial emissions with sulphur dioxide, nitrogen oxides, acid gases, ammonia, amine and oxidizing gases and vapors increase the likelihood for metallic corrosion.

Protection from corrosion generally involves these considerations:

a) Positioning identical or electrochemically similar metals and alloys in a given milieu;

b) Preventing contact of electrolytic solutions with the junction between two different metals by application of protective coverings, coatings or metallic coverings; and c) Cathodic protection can prevent corrosion of metals exposed to an electrolytic environment by electrically connecting the corrodible metal to a sacrificial anode made of a metal higher in the electromotive series than the metal for protection, i.e., a metal that is anodic to the material for protection. When the protected metal and the electrically connected sacrificial anode are both disposed within the same electrolytic environment, a galvanic cell is formed in which the protected material is the cathode, whereby metal atoms on the exposed surface of the sacrificial anode are ionized by the surrounding electrolyte and go into solution and the protected metal does not corrode since free electrons are readily available at the surface of that structure to chemically reduce or neutralize positive ions that reach the surface of the protected material.

Various measuring methods have been utilized in the field of protection against corrosion. Impedance spectroscopy, measurement of oxygen, hydrogen and pH value in solution, the redox potential, and weight control of metallic specimens inserted into the medium and determination of resistance.

Electrical resistance measurement is achieved with by insertion of pieces of wire, tubes or disks into the medium and exterior measurements indicating corrosion from the medium are taken. The change, diminution of size of the object, increases the resistance of the metallic specimen and, therefore, directly relates to the loss of metal by corrosion and/or erosion. The date can be converted to unit loss of metal per time unit to provide corrosion rate per year or similar time period.

Disadvantages concomitant with electrical resistance technique include the fact that the specimen itself is subjected to the signal current, for there is no galvanic separation between the metallic specimen and the medium to be measured. Furthermore, wire specimens are unstable and when used in a fluid moving at high rate, special protective devices for the metal specimen are required. Temperature compensation is unreliable due to disparity of the sacrificial and reference specimens. Changes in resistance of the specimens due to diminution of mass are small and range within milli and micro-Ohms. As such, recordation of signals is difficult and readily subject to extraneous influences. Also, the measurements can be erroneous in stronger electrolytes or by existence of electrical conducting depositions on the specimen.

Other modern sensors for corrosion measuring devices are "linear Polarization Probes", "Hydrogen Probes" and probes for impedance spectroscopy.

Recent reports from Russia indicate development of a method for magnetic measurements for the loss of mass due to corrosion of reinforcements in concrete bridge constructions by the use of "SQUID" gradiometers. Only initial tentative experiments have been reported.

The foregoing disclosures, however, have been found unsatisfactory in many respects. The disadvantage of these procedures is that they cannot be used on a technically large scale; they may be unreliable for sensitivity to extraneous influences; they may not be sufficiently durable and require repetitive calibration.

SUMMARY OF THE PRESENT INVENTION

In view of the various limitations and deficiencies in the foregoing prior art, general objects of the present invention are to provide a method and apparatus to determine the loss of mass of metallic material due to corrosion and erosion; under technically difficult conditions and in aggressive media; unimpeded by foreign influences; and, to obtain signal measurements with sufficient signal sizes to expedite the measuring process with highly reproducible results.

These and other goals are achieved by contacting the medium with a specimen within a probe or sensor formed as a core or yoke having a magnetic field from at least one coil with a set current and the probe or sensor set in a constant position in the medium. Corrosion and erosion of the specimen with resultant diminution in mass gives resultant change of at least one magnetic value, preferably inductivity, relative to inductive resistance in the coil of the sensor, whereby the electromagnetic measurement unit can be derived.

Of the above-mentioned probes, the E/R (Electrical Resistance) probes are similar to the M/R (Magnetic Resistance) probes described herein. Function of the probes can be contrasted as follows:

E/R probes: Loss of metal by corrosion or erosion gives increased resistance in Ohms for the sensor-element which is charged with DC current.

M/R probes: Loss of metal by corrosion or erosion of the sensor element results in diminution of inductivity of the sensor coil/specimen system.

Non-electric characteristics of a fluid can influence the resistance of the sensor and, further, such non-electric quantities can also alter the inductivity of the specimen.

The procedure for determining the corrosivity and/or erosivity of fluid media respective to the change of mass of metallic materials such as iron, more specifically steel, which come into or are in contact with fluid media causing erosion and/or erosion especially in a moving or streaming media, whereby testing is achieved by equipment having a composition and/or structure identical or corresponding to the metallic material exposed and held in contact in the fluid media during a given time span and the change, particularly loss of mass, registered and determined as an electrical measurement and devices facilitating the carrying out of this procedure, comprising a sensor or probe having at least one probe, with a core and/or a yoke within the magnetic field of at least one coil, connected or connectible to an alternating current, under constant geometric circumstances, is brought into contact with a fluid media and the change in mass of the probe, especially the reduction due to corrosion and/or erosion is reflected in the change of at least one magnetic quantity, preferably the inductivity respective to the inductive resistance of the system consisting of coils and probe, specifically the sensor's coil response on the sensor's coils, or in an electrical quantity derived from those electromagnetic quantities whereby the corrosivity of a fluid is determined.

DESCRIPTION OF THE PREFERRED EMBODIMENT

Figure 1A:
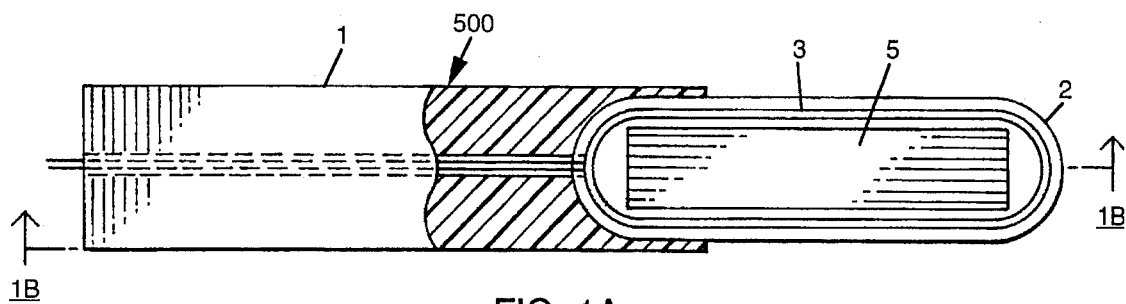
FIG. 1A is a top cross-section along the longitudinal axis of a rectangular probe wherein the coil core is positioned within the metallic specimen support with a fluid tight seal formed by casting.

With regard to receptors sensitive to inductivity, it is recognized that inductance L of a coil is the quantity to be measured electrically. This quantity is dependent on the square of the number of turns N and the reluctance RM of the coil:

$$L = \frac{N2}{RM}$$

The reluctance of a coil surrounded by iron is the length of the wave s of the field lines, divided by the plane A multiplied by the magnetic field constant μo×the degree of permeability μr.

$$RM = \frac{s}{\mu o \times \mu r \times A}$$

The quantity which influences the inductive receptor described herein is the length of the wave s and the degree of permeability μr.

In a simplified form, an inductive probe to serve as the corrosion measuring probe consists of a coil wrapped on a spool or core n iron core which is the specimen which changes external measurements by corrosion or erosion.

The magnetic field lines run in three different areas, namely within the iron (sFe, AFe), in the air within the coil (s,A), and finally upon their return in the air exterior to the coil (sa, Aa). The magnetic resistance of the sensor is:

$$RM = \frac{sFe}{\mu o \times \mu r + AFe} + \frac{s}{\mu o \times A} + \frac{sa}{\mu o \times Aa}$$

The first term on the right side of the equation is very much smaller due to the degree of permeability μr of the iron in the denominator having a value of 1.000 to 10,000 and can thus be neglected. Also the third term can be neglected as the section area Aa available for the return wave is much bigger than the plane A inside the coil. In certain cases it is also possible to cover the coil with soft iron, within which the field lines would run practically without resistance. Therefore, only the iron free distance s within the coil is relevant for the reluctance, expressed as:

$$RM = \frac{s}{\mu O^* A}$$

and the inductance of the probe, expressed $$L = \frac{\mu^* A^* N^* N}{s} = \frac{k}{s} \text{ with } k = \mu o^* A^* N^* N$$

is lower, the more the iron-core (metallic specimen) inside the coil is diminished by corrosion or erosion. It depends on the iron-free distance s in the denominator, whereby the characteristic record of findings forms a hyperbolic shaped line. Sensitivity $$E = -\frac{dL}{ds} = -\frac{\mu_o * A * N * N *}{s * s} = -\frac{L}{s}$$

is also reduced with the increase of s. The relative change of the inductivity and relative change of the wave are identical with reversed premises, as the foregoing equation can be restated and expressed:

$$\frac{dL}{L} = -\frac{ds}{s}$$

The theory of the new corrosion measuring method having been explained, the following discussion will serve to differentiate the invention from former technology and to show advantages over the known state of engineering in this field.

The essential advantages of the new technology over the former method, direct resistance measurement on the specimen itself, include the following.

The inductive resistance is extensively indifferent to variations or gradients of temperature. In order to consider the interference factors due to the dependence on temperature of the direct current which are low in comparison to the level of the measuring signal which is delivered by the sensor in this method, the same can be determined easily by using direct current in the coil of the sensor and making appropriate compensation. The sensor being disclosed herein is indifferent to irregular corrosion, for the mass of the metallic specimen can be influenced by magnetic fields, particularly iron, which is disposed so that the coil is under the influence of the magnetic field and the changes of its mass are determined; whereas for E/R measurements, the sectional area of a wire loop can differ greatly dependent on length because of pitting corrosion.

The precision, sensitivity and resolution of the new method for measurement is approximately 1,000 times greater vis-a-vis the changes of direct current resistance used in the E/R measurements method prevalent in the prior art.

In the method of my invention, electrically conductive depositions from the fluid are irrelevant, since there is no contact between the medium and the electric coil. Furthermore, magnetic measurements are taken and not a direct resistance of the specimen itself.

The galvanic isolation of the conducting coil from the fluid medium reduces danger from explosion. Also, the cathodic protection against corrosion is not disrupted by my method. And my method enables optimized measuring results, because influences dependent on design and dimension of the specimen, coil and sensor, and influences due to alternating current as well as those influences inherent in the medium itself can be respected from case to case at a constant measuring range, particularly by choosing the corresponding frequency. This characteristic of my method leads to improved computation of measuring data, for a large part of the measuring range can always be used.

Due to durably constructed probes and their magnetic sensors, a large range of applications in the field of corrosion control and protection against corrosion can be considered.

Furthermore, the following advantages of the new method can be named. The method can also be used for electrolytes which are non-continuing with low ionic content, for the process provides a linear curve for inductivity relevant to corrosion. The method enhances opportunity for calibration gauging with weight measurement. All current carrying conducting elements of my device are sealed against contact with the corrosive fluid medium.

If the diminution of the metallic mass by corrosion is exceeded, the energy or power supply for the sensor can be automatically shut down. This represents an additional security particularly in explosive media. Such a shut off or shut down will gives clear indication that the entire probe has to be replaced.

Due to the high flexibility and adaptability of the method, forms and dimensions of specimens now in use as well as wall openings to containers and pipelines can remain in use; and, my method thereby allows adaptive optimization of measuring without requiring any construction changes.

A disadvantage which will be minimized in practice when the method is used inside metallic pipeline and container systems should be mentioned. The new method is sensitive to strong exterior magnetic fields and, therefore, respective shielding may be necessary.

Practical use of the new method and the device will be for fluid media conducting and/or storing/stocking systems, whereas the fluid media can range from highly concentrated electrolytic solutions, acids, bases, complex molecules, organic acids, from saline solutions up to weak electrolytes, such as tap water or other water, organically stressed waters, waters conducting abrasive sands or mud, turbid waters, suspensions and organic and biogen liquids and emulsions, such as petroleum, oils, organic solvents, agricultural liquids, such as milk, stals, washing waters and the like, and finally gas, including hot gases, waste gas, smoke, dust with acid or alkali and/or reductive or oxidative characteristics.

My method is of special interest with regard to components which are exposed to corrosive fluids and those which contain and conduct fluids, such as containers and pipeline walls, fittings, ventilators, valves, etc.

These parts are primarily made of metals or alloys of ferromagnetic or materials influenceable by magnetic fields, especially iron based materials and steel products.

As an example for characteristic magnetic dimensions, the density of field lines or susceptibility of the field can be designated; the field size relative to changes of specimen mass by, for example, mounting hall effect devices, chips sensitive to magnetic fields or "squids" into the coil/specimen-system, whereby the field dimension, density and size can be calculated.

It is preferable, particularly with regard to an optimal measuring or corresponding loss of mass of the actual corrosion by the sensor system used and the corrosive medium and the components exposed to it, to expose the coil of the sensor to a preferably sinusoidal alternating current with a frequency in the range of 100 to 300s−1, more preferably from 150 to 250s−1.

In order to determine the loss of mass of a specimen due to corrosive effect of an aggressive medium and to allow exact conclusions on the rate of corrosion, it is advantageous to compensate for external influences, particularly those due to temperature, to sequentially set the coil specimen system of the sensor under direct current to obtain the Ohmic direct current resistance or a similar electric/magnetic measuring figure. And by using the alternating current, it is advantageous to then obtain data for total resistance or a similar electric/magnetic measuring figure; and, by calculating the difference between both resistance values, the inductivity of the coil specimen system respective to its changes or a corresponding measuring figure is determined.

When the coil probe device is used under conditions of magnetic saturation, the range of magnetization has no upward limit and high flexibility of measuring is guaranteed.

According to the prevailing flux conditions within the receptacle, container, basin, tank, or pipeline where corrosion is to be controlled, it is advantageous to position the sensor and its specimen parallel with, or normal to, the flow direction of the fluid media.

Another important subject of the invention is a device for the determination of the corrosivity and/or erosivity of fluid media, by the change of mass of metallic material contacted by fluids causing corrosion, particularly moving fluid media. The device is especially based on iron, particularly steel, with at least one sensor, the sensor having at least one specimen which is identical or corresponding in its composition and/or structure to the above-mentioned material, which material is introduced into the fluid medium during a given time span. The device of the invention is supplied with electric current and includes a device for the determination of a change, especially loss, of the electric measuring figure corresponding to the mass of the specimen, especially for the performance of the a.m. procedure.

The invention is characterized by a device having at least one probe having one sensor with at least one specimen, preferably as a core and/or yoke, within the magnetic field, with at least one coil supplied with and conducting alternating current at a predetermined frequency, form and level of amplitude; and, at least one device connected with the coil specimen system of the sensor for the determination of its magnetic size of core, especially its inductance, particularly inductive resistance.

The device of the invention is preferably constructed to allow for an integrated statement about the change of mass due to the corrosion of underground components, for example the moving fluid medium in a pipeline or the like, the device being positioned at right angles to the direction of the fluid flow.

If a measurement should take place on a surface being in the direction of the moving fluid, a probe having a sensor support in the form of a stick with a measuring sensor mounted on the distal end of the stick crosswise to the axis of the probe with a flat round disc formation and arranged windings in the support of the specimen integrated tight to the medium, preferably flat induction coil, is advantageous.

It should be mentioned here that is possible that the described corrosion sensors used in the specimens due to the described flexible design can also be commercial probes and sensors actually in use, that is the s.m E/R sensors, furthermore forms and measurements corresponding to the common "coupon" trial lamellas, i.e., rectangular or round lamellas.

Another advantageous form of construction designed for hydrodynamics is achieved with a cylindrical specimen.

With a specially favorable design of a coil with a core inside of the sensor with a cylindrical specimen, very distinct differences of signal heights, whereby higher precision of the measuring results can be achieved.

If it is possible in any with regard to the condition of temperature and medium also in view of a simpler and thus less costly design, which also guarantees a high flexibility concerning the form, design and dimension of the coil itself and the positioning of the specimen and also fo the support of the sensor, the use of medium internal, permeable and thermostable material, for example, based on silicate, especially polymers or synthetic material is advantageous.

The following synthetic materials are for example recommended: polypropylene, acrylic resins, alcydic resins and especially epoxy resins.

In order to reduce the risk of corrosion and erosion of the support for the specimen, it is advisable that the specimen and probe supports consist of synthetic material with a corrosion and/or erosion inert layer and/or armoring made of hard ceramic material.

Preservation of the tightness of the construction against aggression of the medium and thus the galvanic separation of the coil and the fluid, it is very advantageous, if the coil and/or the specimen is cast in to the mass of the support of the sensor/specimen.

For this reason, it is advantageous to provide a strong adhesion between the surface of the specimen and the windings of the coil to be bedded fluid tight and the fluid polymer, when bedding the coil and/or specimen into the hardening synthetic material and to prevent it from shrinking during the end of polymerization for hardening of the masses.

The a.m. form of construction with a support of the probe in the form of a hollow stick, which facilitates on the one hand the positioning of the specimen in the defined zone of the cross-section of a fluid-conducting element, and on the other hand also facilitates the mounting from outside, is especially advantageous in view of the mechanical preservation and fluid tightness, if the supply and/or control conductors of the sensor and the coil specimen system and its measuring data conductors traverse through the support of the probe, particularly through a hollow of same.

The advantage is especially relevant if the support of the probe contains more than one corrosion measuring probe and therefore a bundle of conductors.

Another relevant advantage is a form of construction allowing a direct exchange of hitherto used and actually used E/R probes or probes allowing the weighing of "coupons" in which the support of the sensor with the sensor is built in into a fitting, especially screw fitting, which is compatible with a standardized commercial and/or existing penetration of the container or pipeline wall and is preferably pressure proof, tight and insoluble.

With these reliable and also in highly pressureproof versions of available penetration fittings the mounting of the new magnetic measuring sensors into a fluid is possible without modification of existing facilities becomes easily feasible.

In order to determine the corrosivity and/or corrosion profiles in fluids or fluid streams, another advantageous design for the device of the invention has been developed. The support of sensors holds at least two measuring sensors which are disposed a distance from each other and which sometimes have different features.

A supervision, control and adjustment of the measuring data collecting and processing device adjusting itself, which can also be used for other inductance measurements, but has been especially developed for the present procedure and the new device in relation with the present invention and the probes and sensors used in relation with the same, which is especially suitable due to its simple and robust construction, is characterized by a system to be measured in relation to its inductance, especially of the coil specimen system, respectively of the coil of the sensor, is integrated in a preferably closed tension, respectively current supply, measurement and control circuit, which consists mainly in a microprocessor with a control and measurement data collecting and processing program for the output of direct and alternating current with adjustable frequency, form and level of amplitude, preferably in a digitized form, containing a digital-to-analog converter connected with it by the same supply and control conductors, which at its output, is connected through the supply conductor with a controllable analog switch by means of the microprocessor, preferably via a resistor and buffer amplifier, connected to the magnetically sensing, especially inductive, coil specimen system, especially to the coil of the sensor, so that the coil, preferably voltage dropping, with a measurement amplifier, preferably 1:1, is connected on its side with a—in cases multistage differential amplifier, that the entry of the differential amplifier is further connected over a reference line branched off at the switch, with a sample-and-hold device for storage and output of a reference voltage, which has been provided by the microprocessor, to the differential amplifier and that finally the differential amplifier is connected to the microprocessor on its output, preferably over an analog-to-digital converter and a conductor for measuring data and control.

There is a strong relation between the invented procedure and the components, which are designed for it and described above, and the hitherto used method of direct definition of the change of mass, especially the loss of mass of corrosion specimens in form of lamellas or disks or the like and the revolutionary variation of the invention necessitating no adaption of the measuring stations themselves where the inductivity sensor is not placed inside the corrosive medium, but exterior to it, thus replacing a scale, for example in a test laboratory, and can be built into the specimen which up to now had to be weighed, whereas the mass respective to change of the mass is determined by means of an inductance measurement and the new device can advantageously be integrated into the above described supply, control and measurement device and thus replace the above described in-situ probe.

The new device for the determination of the mass respective to mass change, especially "coupons", of specimens exposed to corrosive and/or erosive fluids is characterized by at least one, preferably disposed in a shielded housing and by means of conductors with alternating current supplied to the coil, inside of which a support is mounted for an exactly positioned, reproducible reception of a corroded probe with specimen, especially "coupons" and at least one device connected to the coil for supply of the same with current, particularly alternating current, with programmable frequency, form and range of amplitude and at least one device, which is also connected to the coil specimen system for the determination of at least one of its magnetic core sized, especially of its inductance with respective to its inductive resistance.

This helps also to speed up the reliable standardized technique of weighing of the corrosion control.

Referring now to the drawing, FIGS. 1A, 1B, 2A, 2B and 3A, 3B, show respectively the top and side cross-section views of the embodiments of in-situ probes and their sensors according to the invention. Thus, several embodiments of the present invention are shown the Figures. The probes 500, in the order of the foregoing figures are disclosed as rectangular FIGS. 1A, 1B; or round as in FIGS. 2A, 2B; or lamella-like and cylindric, closed on one end, form of the specimen as in FIG. 5. On each distal end of the respective sensor-supports formed as a stick, a cylindrical support for the specimen 5 to be introduced into the fluid medium in the following forms:

rectangular, oval (favorable in the fluid stream), crosswise to the streaming direction;
round, disc-shaped, to be positioned approximately in the streaming direction (parallel the direction) of the medium;

is mounted, whereas the cavity within the support 2 is mounted in a sheathing and the specimen 5 in a fluid tight way, (for example sealed by casting) and inside the specimen support 1, (See FIG. 1), the coil 3, preferably a flat coil 3, carries electric current, preferably alternating (AC) current, by means of a conductor (not shown), which conductors are sealed, the openings for the introduction of the coil of the embodiments shown in FIGS. 1A,1B and 2A,2B are sealed with the sealing element 4.

Figure 3A:
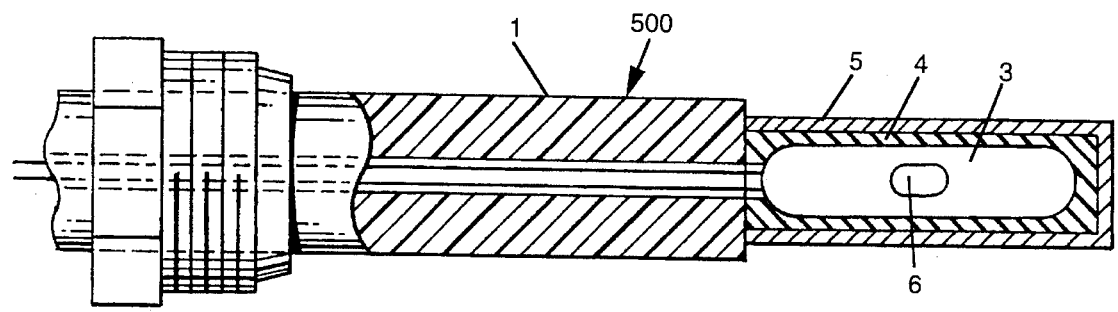
FIG. 3A is a top cross-section along the longitudinal axis of a probe compatible with a screw fitting for a standard wall penetration system, wherein the coil core is centrally within the cylindric metal specimen.
Figure 3B:
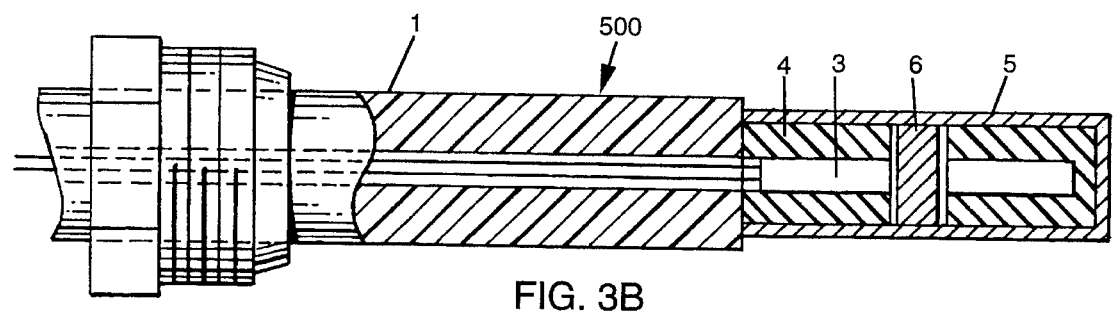
FIG. 3B is a side cross-section of the probe of FIG. 3A.

FIGS. 3A,3B show how probe 500 may be formed and adapted to be fixed into a compatible screw fitting for a standard wall penetration system. In addition, probe 500 in FIGS. 3A,3B shows a central coil core, which is tightly connected to the inside of the cylindric specimen 5, thereby essentially forming a core yoke system.

Figure 4:
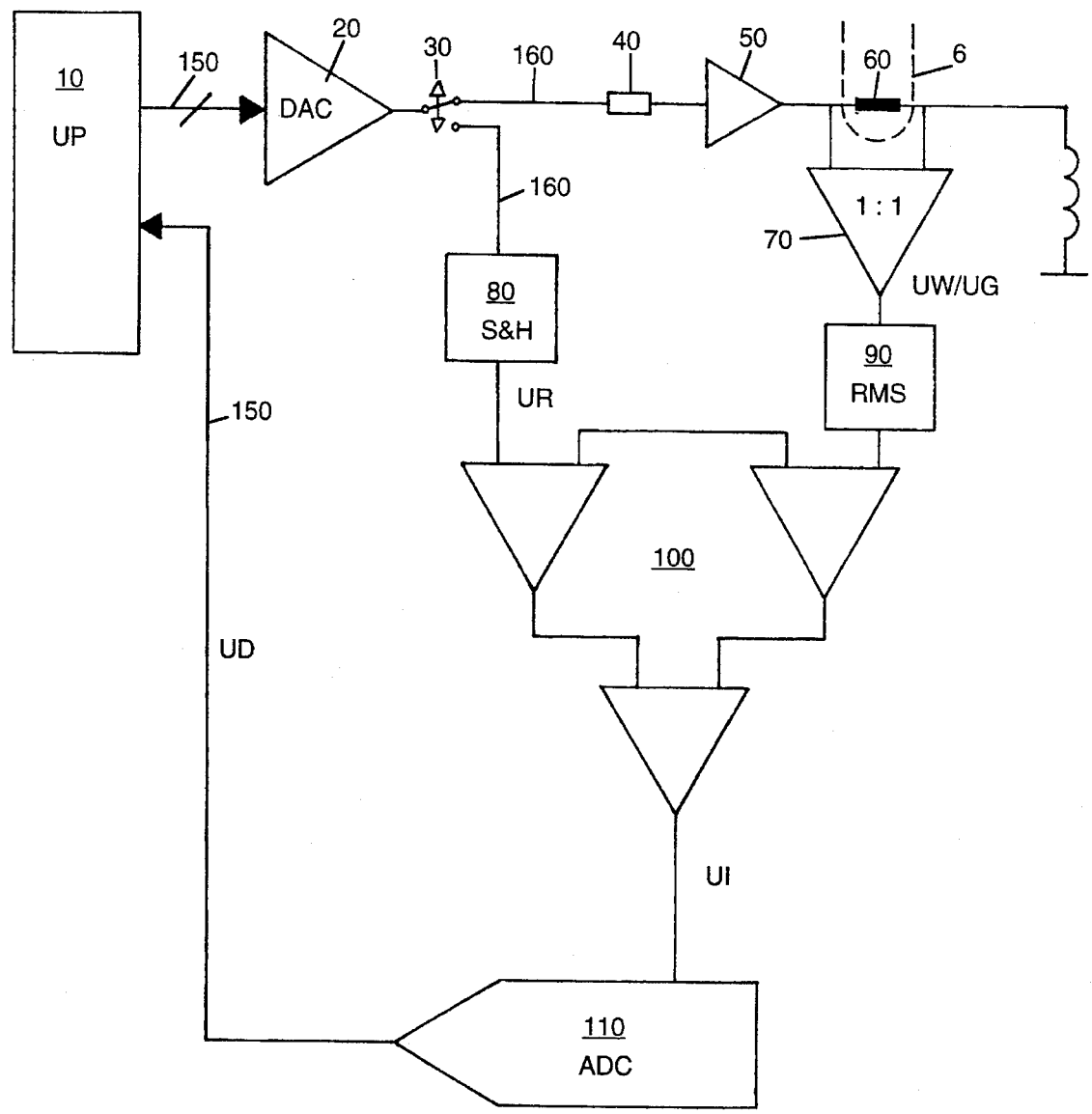
FIG. 4 is a schematic diagram of the new corrosion control device of the invention, wherein a multifunctional microprocessor supplies a digital analog converter whereby the frequency, form and range of amplitude and alternating current are adjusted for measurement and configuration of the measuring instruments; the analoguized data transported by a switch to a resistor and an amplifying buffer into a coil of the coil metal specimen system of the magnetic sensor contacting the corrosive fluid whereby the specimen sustains loss of mass.

FIG. 4 is a schematic diagram of the device according to the invention with dispositions for supply, control and measurements.

FIG. 4 shows the preferred embodiment of the new corrosion control device. The multifunctional microprocessor 10 configures the system for measurement by providing a synthesized sinusoidal waveform, of predetermined amplitude and frequency over a predetermined frequency range for the principal mode of operation and by providing a stable DC voltage for the measurement of the electrical resistance.

To establish the reference voltage $U_r$, the multifunctional microprocessor 10 provides a digital word to the digital-to-analog converter 20 via a multiconductor cable 150, to the input of a computer selectable multiplexer 30. With the reference mode selected, the output of multiplexer 30 is connected to Sample-and-Hold Device 80 via conductor 180. The output of the Sample-and-Hold Device 80 connects to the (−) input of differential amplifier 100, where the reference voltage $U_r$ is established.

In the principal measurement mode, the output of multiplexer 30 is connected serially to resistor 40 and buffer amplifier 50 via conductor 160. The output of buffer amplifier 50 is serially connected to coil 60 of the previously described coil specimen System of the magnetic sensor 6. Magnetic sensor 6 is normally in contact with the corrosive fluid and suffers the loss of mass. It is shown here in a dashed line.

The voltage drop that appears across coil 60 is isolated the 1:1 measurement amplifier 70. Its output is designated as $U_w$. This measured voltage drop corresponds to the product of the coil impedance and the current that flows through it.

In the second mode of measurement, the microprocessor 10 supplies a constant predetermined DC voltage from the digital-to-analog converter 20 via multiplexer 30, resistor 40 and buffer amplifier 50 to provides a DC current through coil 60. This is a measure of the pure ohmic DC resistance of the sensor system. This DC voltage drop across coil 60 is measured by the instrumentation amplifier 70 and appears at its output as voltage $U_g$.

The output of instrumentation amplifier 70 has both values of the voltage drops, $U_w$ and $U_g$, which resulted sequentially first from the application of an alternating waveform, then from an applied DC direct current. This output signal is passed on to RMS converter 90, which converts the sinusoidal waveform to a DC voltage corresponding to the rms value of that waveform. The output of RMS converter 90 is then directed to the (+) input of differential amplifier 100.

Appearing at the output of differential amplifier 100 is voltage $U_i$ which is the difference between voltages $U_w$ and $U_r$. This output voltage then corresponds to the inductive reactance of the coil 60. The voltage $U_i$ is digitized by the analog-to-digital converter (ADC) 110, where is output connects via a multiconductor cable 150 to the digital input of microprocessor 10. If different values appear between reference voltage UR and temperature compensated reactive voltage UI, this difference signal UD is transmitted to microprocessor 10 which does the measurement itself, via the ADC analog digital converter 110 with 20,000 steps and conductor 150. The microprocessor 10 carries out the adaption of the reference voltage according to the difference of the signal UD as long as the difference of the signal UD with which it has been supplied, equals zero.

If there is a loss of mass of a specimen of probe 6, this changes its inductivity, and also the taped UW, the resulting voltage UI and an adjustment of the signal by the microprocessor for the reference current UR has to take place due to the difference signal, UD, coming through via the feedback control conductor 150.

The number of adjustment steps per unit time respective to the change of the reference current UR is a measure of the change of mass, caused by the corrosion of the specimen, which can then be easily determined. Consequently a device is provided having a closed control loop, being universally applicable.

Figure 5:
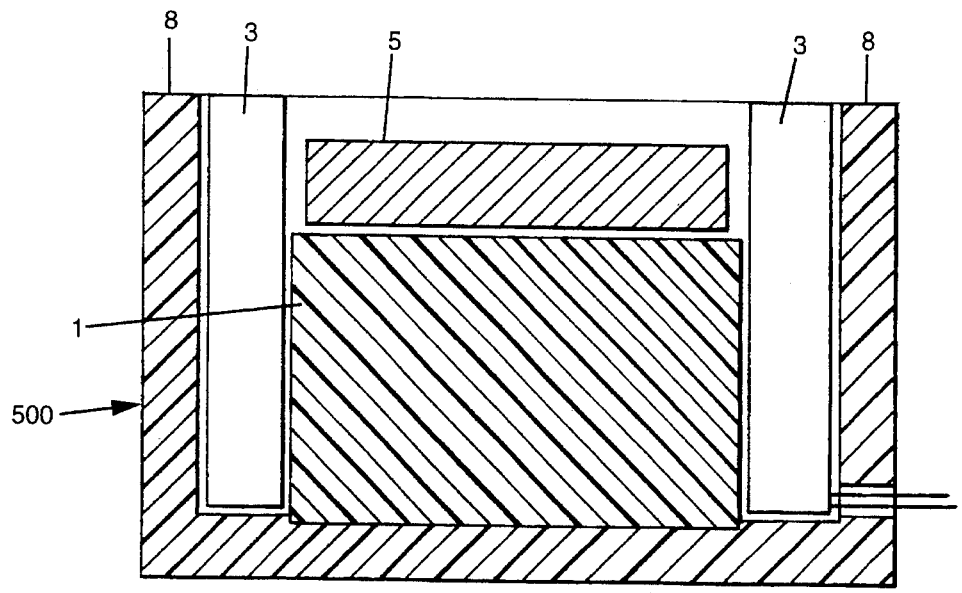
FIG. 5 is a side cross-section of a specialized embodiment of the invention suitable to measure the loss of mass of the specimen, known as "coupon", that metallic specimen positioned transversely within the charged coil, but although differently dimensioned and configured, is operative identically as the inductivity probes shown in FIGS. 1–3 above.

The device shown in FIG. 5 is a special variant of the invention and is suitable for the determination of the loss of mass of a specimen 5, also called "coupon" 5, which has been taken out of a corroding system where it has been exposed itself or a time span to the medium and represents a probe 500 outside of the corrosive medium. Its sensor 100 is, even if differently dimensioned and configured, completely identical to the inductance probes heretofore described.

In a shielding housing 6 is a coil 3, which is supplied with alternating current through a conductor (not shown), on the inner side of which housing a highly reproducible coupon 5 is mounted inside of coil 3, whereby coupon 5 represents here a "coil core" which is heavily altering the coil inductance 3 by its change of mass due to corrosion. Suitably this dry sensor 500 is integrated into a device in accordance with FIG. 4.

Figure 1B:
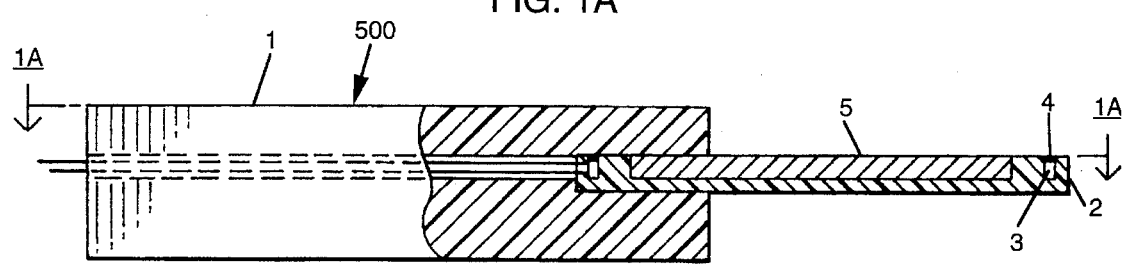
FIG. 1B is a side cross-section along the longitudinal axis of the probe shown in FIG. 1A.

This probe 500 for the embodiment of FIG. 1A and FIG. 1B is comprised of an insulated hollow handle 1, which has a cavity as shown running through the length of its central portion. This longitudinal cavity serves as a conduit through which coil leads (not shown) are run. The flat rectangular sacrificial element 5 (also referred to as the specimen) is centered within the ovately wound coil 3. The coil and sacrificial element are encapsulated ovately with an Epoxy or silicone encapsulant 2 and the coil 3 is also protected by non-corrosive seal 4. In this embodiment, the surface of sacrificial anode is fully exposed to the environment whose corrosivity it is adapted to measure. In typical use, when immersed in a fluid medium, if the flow stream is directed toward or orthogonal to the surface of the sacrificial anode, it is positioned for the best measurement of erosion. If the flow stream is tangential to anode surface, it is in position for the best measurement of corrosivity.

Figure 2A:
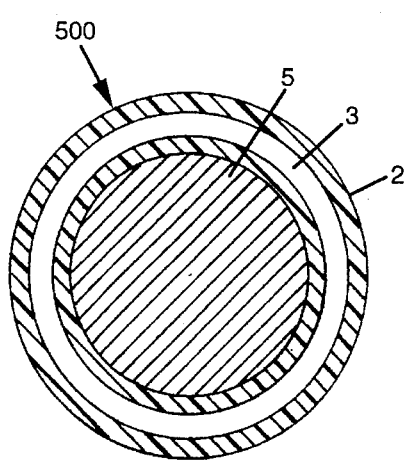
FIG. 2A is a top elevation of a round or disc-shaped probe to be positioned parallel with the direction of a moving fluid.
Figure 2B:
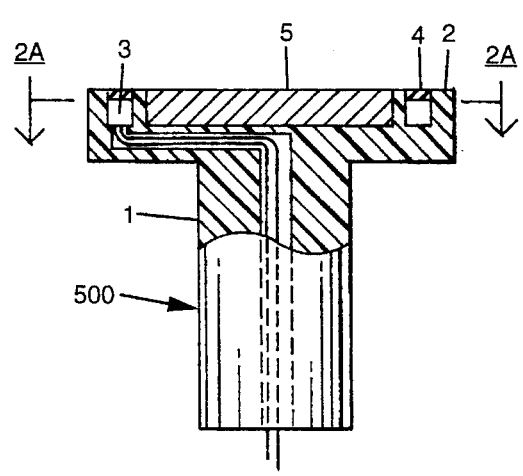
FIG. 2B is a side cross-section view of the round or disc-shaped embodiment for the probe of FIG. 2A.

The Probe 500 shown in FIG. 2A and FIG. 2B are the top and side cross-section views of an alternative embodiment for the present invention. Depicted is a circular disk shaped (lameliar) sacrificial specimen 5, which is centered within the circularly wound coil 3. In this embodiment, the coil is recessed within the encapsulant 2 and subsequently protected from the fluid medium by the insulated layer of seal 4. The entire assembly is attached to the hollow handle 1. The sacrificial element again has one side exposed to the fluid medium. The use of this embodiment is the same as was discussed for the embodiment shown in FIG. 1A and FIG. 1B in the preceding paragraph.

FIG. 3A and FIG. 3B are still another embodiment for this invention; FIG. 3A is the top cross-section along the longitudinal axis and FIG. 3B is the side cross-section of the same. In this embodiment it is designed to be compatible with a screw fitting for a standard used system. Again, the coil 3 is a flatly wound rectangular shaped coil (racetrack shaped). Centrally mounted within the coil is a metallic core 6 to transport the lines of flux to the outer cylindrical shell which in this embodiment is the sacrificial anode or specimen. An encapsulant 4, such as a potting compound is used to protect the coil from being corroded by the fluid medium.

FIG. 5 is a side cross-section along the longitudinal axis of a specialized embodiment that uses the principles of the present invention. The coil assembly is essentially shielded by the enclosure 8. Within this enclosure is the coil 3, the insulated specimen support 1, and the specimen 5. The loss of mass is determined in the same manner as discussed below.

Regarding the process of corrosion, corrosion is the action, process or effect of corroding. Typically, it is a gradual wearing away or alteration by a chemical or electrochemical being essentially an oxidizing process, as in the atmospheric rusting of iron.

Erosion is produced commonly referred to as the gradual progressive loss or surface destruction of a hard substance through abrasive action. Chemically, erosion occurs through the abrasive action of a moving fluid or gas, and is accelerated by particles that are held in suspension.

There are many geometrical configurations that can be used in the principles discussed and for the four examples that are shown. Basically, the coil induces a sinusoidal voltage into the metallic core. Specifically, in FIG. 1, 2 and 5, these induced sinusoidal voltages cause a circulating current to flow circularly within the sacrificial anode, The path and current density within this core are functional with the applied frequency. For example, the higher the frequency. the closer to the surface of the circular path is taken by these circulating currents. Conversely ribs the lower the frequency of excitation, the greater is the depth of the circulating currents. These circulating currents are more commonly referred to Eddy currents.

These circulating currents in turn give rise to counter emf's that oppose the initial direction, thereby yielding a resultant change in inductance, which provides an extremely sensitive measurement of corrosion or erosion caused by the reduction or loss of metal within the specimen or sacrificial anode.

Specifically, the loss of mass is easily determined by the change of inductance as detected by the coil. This loss of mass is a direct measure of the corrosion or erosion that had taken place. For example, when the system is first placed in operation, an initial measurement of the inductance is made. After several hours of operation, another reading of the inductance is made. Perhaps the measurements need only be taken after several days or even months, depending upon the corrosivity of the fluid medium. These changes of inductance are then a direct measure of the loss of metal within the metallic specimen which is inversely proportional to the rate of change of corrosivity and/or erosivity.

With reference to the embodiment shown in FIG. 3, the coil is surrounded by a cylindrically shaped canister that acts as the sacrificial anode, Even though this embodiment is slightly less sensitive, the coil assembly is metallically shielded which protects the sensor from extraneously induced objectionable interferences.

In all cases, the coil structure must be encapsulated to protect it from the corrosive environment. Should the coil become corroded, the subsequent measurements would be in error, as well as to cause damage to the coil itself.

Restating again the measure of corrosion is best determined by placing the probe in the fluid stream so that the flow is tangential to the surface or the sacrificial anode. It is also true that best measure of erosion can be obtained when the fluid flow is directed towards or orthogonal to the surface of the sacrificial anode. However the probe embodiment of FIG. 3 is best suited in applications where there may be corrosive and erosive chemical actions present.

Two principal measurements are made to determine the corrosivity and/or erosivity. They are: (1) the DC ohmic resistance, R, of the coil and (2) the impedance, Z, of the coil In the measurement of the DC resistance of the coil, a steady state direct current voltage is applied as the excitation to the probe coil. The current that flows through the coil is sensed by the voltage drop across the current sensing resistor. It then follows that:

$$R_{dc} = \frac{E_{dc}}{I_{dc}}$$

To determine the impedance Z of the coil, a steady state sinusoidal voltage, of frequency f is then applied as the excitation to the probe coil. Therefore:

$$Z = \frac{V_{ac}}{I_{ac}}$$

and $Z = SQRT(R2 + (xL2))$

Because the changes of inductance, L are a direct measure of the loss of metal within the metallic specimen, it then follows:

$X1 = SQRT(Z2 - R2)$ and $$L = \frac{X1}{2*Pi*f}$$

which is inversely proportional to the rate of change of corrosivity and/or erosivity.

The invention is not limited to the details disclosed since many changes and modifications are possible without departing in any way from the spirit of the invention. What is desired to be protected by Letters Patent is set forth in the appended claims.

What is claimed is:

1. A method to determine the corrosivity and erosivity of a fluid media respective to the change of mass of a metallic material contacting the fluid media, comprising the steps of:

providing a probe comprising a support member with a metallic specimen fixed to the support, the specimen comprising a metallic material; said probe further having an at least one coil mounted on the support, the at least one coil connected to a voltage source for creating a magnetic field around each coil; and said specimen held in a permanently fixed position within the magnetic field of the at least one coil;

contacting the specimen with a fluid media;

determining a diminution of a coil inductance; and, determining a reduction of mass of the metallic specimen due to corrosion respective to the diminution of the coil inductance.

2. The method of claim 1, wherein said voltage source which is applied to the coil comprises an alternating current having a sine wave form with a frequency range from 100 to 300 Hz.

3. The method of claim 1, wherein said voltage source comprises a sine wave alternating current which is applied to the coil, the sine wave having a frequency range from 150 to 250 Hz.

4. The method of claim 1, further comprising the steps of:

applying a direct current source to the coil to determine an ohmic resistance of the coil; and, applying an alternating current source to the coil, alternately to the direct current application, to determine the actual value of the total effective resistance of the coil; and, determining the coil inductance by the difference between the two alternate quantities.

5. The method of claim 4, wherein the specimen of the probe is subjected to a controlled magnetic saturation.

6. The method of claim 5, wherein the probe and the specimen comprise a sensor having a main axis and the fluid media has a flow direction; and, said main axis of the sensor is positioned normal to the direction of flow of the fluid media.

7. The method of claim 5, wherein the probe and the specimen comprise a sensor having a main axis and the fluid media has a flow direction; and, the main axis of the sensor is positioned parallel to a flow direction of the fluid media.

8. A system to determine the corrosivity and erosivity of a fluid media respective to the change of mass of a metallic material contacting the fluid media to cause corrosion, comprising:

a core comprising a metallic material having a mass to contact the fluid media during a given time span;

a coil positioned in proximity to the core;

a means for supplying the system with electrical current to the coil for creating a magnetic field around the coil;

the core held in a fixed position within the magnetic field; and, a means to measure changes, specifically a loss of the mass of the core, by evaluating changes in electromagnetic properties of the system.

9. The system of claim 8, wherein the electromagnetic property determined by the system is an inductance of the coil.

10. The system of claim 9, wherein the probe further comprises an axis of the probe and a sensor support formed as a rod having a proximal end and a distal end, with a measuring sensor mounted on the distal end thereof and positioned to point in the direction of the axis of the probe;

the probe further comprising a support of the core with a recessed area within the support which is encapsulated in a watertight material, allowing access of the probe to the fluid medium with the core only contacting the fluid; and the coil having arranged windings formed as a flat induction coil positioned within the support of the core and sealed tightly within the recessed area and within the watertight material of the probe support.

11. The system of claim 10, wherein the core comprises an iron material which is encased within the coil and extends crosswise to the axis of the support and is fixed within the inside of the support.

12. The system of claim 10, further comprising the support of the core formed as a cylindrical rod, with the core itself forming an outer surface of the probe, said support closed on the proximal end and said flat coil sealed tightly in the watertight material and thereby integrated into the support.

13. The system of claim 12, wherein the support is constructed of a thermo-stable material.

14. The system of claim 13, wherein the support is constructed of a corrosion inert layer.

15. The system of claim 14, wherein the corrosion inert layer is a hard ceramic material.

16. The system of claim 10, wherein the sensor support is integrally formed with a screw fitting, said fitting compatible with a standard commercial fitting.

17. The system of claim 10, further comprising a plurality of sensor and data measuring conductors which traverse through the hollow portion of the sensor support.

18. The system of claim 17, further comprising the sensor support having at least two measuring sensors, said at least two measuring sensors having different construction and mounted on the support a distance from each other.

19. The system of claim 17, wherein the system measures inductance of the coil; said coil is integrated into a closed, current conducting, measuring and control circuit, which communicates with a microprocessor, the microprocessor having a control and measuring data, collecting and processing program, for the supply of both direct and alternating currents in a predetermined frequency, amplitude, digitized waveform, and range;

the microprocessor is in further communication with a digital-to-analog converter, having a converter output through supply and control conductors;

the converter output communicates to a controllable analog-switch and to a supply conductor, via a resistance and buffer amplifier, with a magnetic sensor sensing a voltage across, the coil;

the coil is in further communication via a measurement amplifier, which is a 1:1 measurement amplifier having an exit side and an entry side;

the amplifier exit side in communication with an effective value (rms) converter for alternating current, which converter further communicates to a difference, multi-staged amplifier;

the entry side of the amplifier communicates with the sample-and-hold switch for the storage and output of one of the reference voltages delivered by the microprocessor to the amplifier; and, the amplifier communicates on its output to the microprocessor via a digital-to-analog converter and a conductor for measuring data and control.

20. The system of claim 19, wherein at least one coil is disposed in a shielded housing and supplied with an alternating current via conductors;

said housing provides a sealed watertight support for the corrosion probe core and at least one device connected to the coil for the supply of this system with an alternating current of a predefined frequency, amplitude, waveform and range, and at least one device also connected to the coil and core system for the determination of at least one of its magnetic core properties, especially of its inductance respective to its inductive reactance.

21. A system for determining the corrosivity and erosivity of a fluid medium upon metallic materials, comprising:

a probe comprising a coil and a core positioned near the coil, the core having a mass and comprising a metallic material contacting the fluid medium whose corrosivity and erosivity is to be determined;

a voltage source in communication with the coil;

a means for applying a direct current followed by an alternating current to the coil, thereby creating a magnetic field about the coil, a magnetic path of the core, a DC resistance, an AC effective resistance, and an original inductance of the coil; and, a means for making sequential measurements of the direct current resistance, the alternating current effective resistance and the inductance of the coil, wherein the measurements are indicative of the corrosivity and erosivity.

22. The system according to claim 21, wherein the means for applying direct current followed by alternating current comprises a microprocessor.

23. The system according to claim 22, wherein the means for sequential measurements comprises an RMS converter.

24. The system according to claim 23, further comprising a means for converting a digital numerical sequence to generate a sine wave analogue voltage.

25. The system according to claim 24, wherein the means for converting comprises a DAC converter.

26. The system according to claim 25, further comprising a means for alternatively selecting between the voltage generation to the coil and to a reference voltage for purposes of calibration.

27. The system according to claim 26, wherein the means for alternatively selecting comprises a switch.

28. The system according to claim 27, further comprising a means for translating the voltage across the coil to a voltage reference to common.

29. The system according to claim 28, wherein the means for translating comprises a one-to-one differential amplifier.

30. The system according to claim 29, further comprising a means to digitize a voltage proportional to the coil inductance to be read by the microprocessor.

31. The system according to claim 30, wherein the means to digitize the voltage proportional to inductance comprises an ADC converter.

32. The system according to claim 31, wherein the means for controlling a magnetic saturation comprises an air gap in the magnetic path of the core, the gap having a distance dimension, such that controlling the gap distance provides resultant control of the magnetic saturation of the core.

33. The system according to claim 31, further comprising a means for controlling a magnetic saturation of the core.

34. The system according to claim 33, wherein said magnetic field induces eddy currents in the core, said eddy currents having a direction.

35. The system according to claim 34, wherein said eddy currents induce a second magnetic field around the core, said second magnetic field having a direction and an intensity.

36. The system according to claim 35, wherein the direction of said second magnetic field is essentially in opposition to the direction of the magnetic field of the core.

37. The system according to claim 36, wherein the intensity of the second magnetic field is dependent on the mass of said core.

38. The system according to claim 37, further comprising a reduction in the core mass by corrosivity and erosivity of the fluid medium contacting the core.

39. The system according to claim 38, further comprising a reduction in said original inductance of the coil consequent to said second magnetic field intensity, and further consequent to said reduction in the core mass.

40. The system according to claim 39, wherein the probe further comprises a handle support.

41. The system according to claim 40, wherein the handle support comprises a tube shape.

42. The system according to claim 40, wherein the coil is encapsulated in a watertight material.

43. The system according to claim 42, wherein the voltage source communicates with the coil through the tube handle.

44. The system according to claim 43, wherein the coil is surrounded by the core mass.

45. The system according to claim 43, wherein the core mass is surrounded by the coil.

* * * * *